US007306902B2

(12) United States Patent
Thompson et al.

(10) Patent No.: US 7,306,902 B2
(45) Date of Patent: Dec. 11, 2007

(54) ONCOLYTIC VIRUSES AS PHENOTYPING AGENTS FOR NEOPLASMS

(75) Inventors: Bradley G. Thompson, Calgary (CA); Matthew C. Coffey, Calgary (CA)

(73) Assignee: Oncolytics Biotech Inc., Calgary, Alberta ( * ) Notice: Subject to any disclaimer, the term of this patent is extended or adjusted under 35 U.S.C. 154(b) by 167 days.

(21) Appl. No.: 10/602,024

(22) Filed: Jun. 24, 2003

(65) Prior Publication Data
US 2004/0029112 A1   Feb. 12, 2004

Related U.S. Application Data

(60) Provisional application No. 60/443,188, filed on Jan. 29, 2003, provisional application No. 60/392,031, filed on Jun. 28, 2002.

(51) Int. Cl.
C12Q 1/70    (2006.01)
A61K 48/00   (2006.01)

(52) U.S. Cl. .............................. 435/5; 435/2; 435/7.21; 514/44; 424/93.1

(58) Field of Classification Search ................ 435/264, 435/325, 42, 5, 2, 7.21
See application file for complete search history.

(56) References Cited

U.S. PATENT DOCUMENTS

| 5,670,330 | A  | * | 9/1997 | Sonenberg et al. | ............ | 435/15 |
| 6,777,177 | B1 | * | 8/2004 | Rubin et al. | .................... | 435/5 |
| 2003/0138405 | A1 | * | 7/2003 | Fueyo et al. | ............... | 424/93.2 |
| 2003/0165465 | A1 | * | 9/2003 | Roberts et al. | ............ | 424/93.2 |

FOREIGN PATENT DOCUMENTS

| EP | 0 931 830 A2 | 7/1999 |
| WO | WO 00/62735 | 10/2000 |
| WO | WO 01/19380 A2 | 3/2001 |
| WO | WO 01/35970 A1 | 5/2001 |
| WO | WO 01/37866 | 5/2001 |
| WO | WO 02/04596 | 1/2002 |
| WO | WO 02/39117 | 5/2002 |

OTHER PUBLICATIONS

Strong, J.E. "The molecular basis of viral oncolysis: usurpation of the Ras signaling pathway by reovirus" EMBO (1998) vol. 17, No, 12, 3351-3362.*
Norman, K.L. "Reovirus as a novel oncolytic agent" J. Clin. Invest. (Apr. 2000) vol. 105, No. 8, 1035-1038.*
Norman et al. "Reovirus Oncolysis of Human Breast Cancer" Hum. Gene. Ther. (Mar. 2002) vol. 13, 641-652.*
Coffey, M.C. "Reovirus Therapy of Tumors with Activated Ras Pathway" Science (Nov. 1998) vol. 282, 1332-1334.*
Hirasawa, K. "Oncolytic Reovirus agains Ovarian and Colon Cancer" Cancer Res. (Mar. 2002) vol. 622, 1696-1701.*
Norman et al. Proc. Natl. Acad. Sci. U S A. Jul. 27, 2004; 101(30): 11099-11104.*
Smith et al. Exp. Opin. Invest. Drugs 2000, vol. 9, No. 2, pp. 311-327.*
Einspahr et al. Cancer Epidemiol. Biomarkers Prev. 2006, vol. 15(8), pp. 1443-1450.*
Norman K.L., et al., "Reovirus Oncolysis of Human Breast Cancer", *Human Gene Therapy* 13(5):641-652 (2002).
Portella, G. et al., "ONYX-015, an E1B Gene-Defective Adenovirus, Induces Cell Death in Human Anaplastic Thyroid Carcinoma Cell Lines", 2002, The Journal of Clinical Endocrinology & Metabolism, vol. 87 (6), pp. 2525-2531.
Bischof JR. et al., "An Adenovirus Mutant that Replicates Selectively in p53-Deficient Human Tumor", *Science* 274(5286):373-376 (1996).
Bos, J, "ras oncogenes in human cancer: a review", *Cancer Res.* 49:4682-4689 (1989).
Campbell, S.L. et al., "Increasing complexity of Ras signaling", *Oncogene* 17: 1395-1413 (1998).
Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998).
Chang et al., *J. Virol.* 69:6605-6608 (1995).
Chang et al., *Proc. Natl. Acad. Sci.* 89:4825-4829 (1992).
Chang et al., *Virol.* 194:537-547 (1993).
Fueyo, J., et al., "A Mutant Oncolytic Adenovirus Targeting the Rb Pathway Produces Anti-Glioma Effect in Vivo", *Oncogene* 19(1):2-12 (2000).

(Continued)

Primary Examiner—Bruce R. Campell
Assistant Examiner—Bao Qun Li
(74) Attorney, Agent, or Firm—Fish & Richardson P.C.

(57) ABSTRACT

The present invention provides a method of diagnosing neoplasms having a particular phenotype by using oncolytic viruses that selectively replicate in neoplasms having the particular phenotype. For example, reovirus does not replicate in normal cells. However, reovirus selectively replicate in cells with an activated ras pathway, which leads to death of these cells. Therefore, a cell which becomes neoplastic due to, at least in part, elevated ras pathway activities can be diagnosed by its susceptibility to reovirus replication. This invention can further be applied, using other oncolytic viruses, to the diagnosis and/or treatment of other tumors, such as interferon-sensitive tumors, p53-deficient tumors and Rb-deficient tumors. Kits useful in the diagnosis or treatment disclosed herein are also provided.

10 Claims, No Drawings

OTHER PUBLICATIONS

Gutkind, J.S., "The pathways connecting G protein-coupled receptors to the nucleus through divergent mitogen-activated protein kinase cascades", *J Biol Chem.* 273:1839-1842 (1998).

Kawagishi-Kobayashi, M. et al., *Mol. Cell. Biol.* 17:4146-4158 (1997).

Nemunaitis, J., "Oncolytic viruses", *J. Invest. New Drugs* 17:375-386 (1999).

Nibert, M.L., Schiff, L.A., and Fields, B.N., "Reoviruses and their replication", pp. 1557-1596 in *Virology* (Fields et al., 3rd Edition), Lippencott-Raven Press, 1996.

Romano et al., *Mol. Cell. Bio.* 18(12):7304-7316 (1998).

Sharp et al., *Virology* 250:302-315 (1998).

Smith, R.E., et al., "Polypeptide components of virions, top component and cores of reovirus type 3", *Virology*, 39:791-800 (1969).

Smith, C.A. et al., "Correlations among p53, Her-2/neu, and ras overexpression and aneuploidy by multiparameter flow cytometry in human breast cancer: evidence for a common phenotypic evolutionary pattern in infiltrating ductal carcinomas", *Clin Cancer Res.* 6(1):112-26 (2000).

* cited by examiner

ONCOLYTIC VIRUSES AS PHENOTYPING AGENTS FOR NEOPLASMS

RELATED APPLICATIONS

This application claims the benefit of U.S. Provisional Applications Ser. No. 60/392,031, filed Jun. 28, 2002; and Serial No. 60/443,188, filed Jan. 29, 2003. The entire disclosure of each of these prior applications is hereby incorporated by reference.

FIELD OF THE INVENTION

This invention relates to methods of detecting the underlying cause of tumors, particularly the use of reovirus in the diagnosis of ras-activated tumors. In addition, other oncolytic viruses with different selectivities can also be used in the diagnosis of particular tumor types.

REFERENCES

U.S. Pat. No. 6,136,307.

WO 94/18992, published Sep. 1, 1994.

Bischoff JR. et al., "An Adenovirus Mutant that Replicates Selectively in p53-Deficient Human Tumor", Science 274(5286):373-376 (1996).

Bos, J, "ras oncogenes in human cancer: a review", Cancer Res. 49:4682-4689 (1989).

Campbell, S. L. et al., "Increasing complexity of Ras signaling", Oncogene 17: 1395-1413 (1998).

Chandron and Nibert, "Protease cleavage of reovirus capsid protein mu1 and mu1C is blocked by alkyl sulfate detergents, yielding a new type of infectious subvirion particle", J. of Virology 72(1):467-75 (1998).

Chang et al., J. Virol. 69:6605-6608 (1995).

Chang et al., Proc. Natl. Acad. Sci. 89:4825-4829 (1992).

Chang et al., Virol. 194:537-547 (1993).

Fueyo, J., et al., "A Mutant Oncolytic Adenovirus Targeting the Rb Pathway Produces Anti-Glioma Effect in Vivo", Oncogene 19(1):2-12 (2000).

Gutkind, J. S., "The pathways connecting G protein-coupled receptors to the nucleus through divergent mitogen-activated protein kinase cascades", J Biol Chem. 273:1839-1842 (1998).

Kawagishi-Kobayashi, M. et al., Mol. Cell. Biol. 17:4146-4158 (1997).

Nemunaitis, J., "Oncolytic viruses", J. Invest. New Drugs 17:375-386 (1999).

Nibert, M. L., Schiff, L. A., and Fields, B. N., "Reoviruses and their replication", pages 1557-96 in Virology (Fields et al., 3rd Edition), Lippencott-Raven Press, 1996.

Romano et al., Mol. Cell. Bio. 18(12):7304-7316 (1998).

Sharp et al., Virology 250:302-315 (1998).

Smith, R. E., et al., "Polypeptide components of virions, top component and cores of reovirus type 3", Virology, 39:791-800 (1969).

Smith, C. A. et al., "Correlations among p53, Her-2/neu, and ras overexpression and aneuploidy by multiparameter flow cytometry in human breast cancer: evidence for a common phenotypic evolutionary pattern in infiltrating ductal carcinomas", Clin Cancer Res. 6(1):112-26 (2000).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

With recent developments in the field of oncology and cell biology, researchers have been able to begin drug development programs that specifically target the underlying cause of cancer, particularly if the cause is the deficiency or mutation of specific gene products. Therefore, if clinicians have the tools to determine the cause of cancer for each cancer patient, a treatment regime can be chosen which is tailored for the specific cause with optimized efficacy.

The ras oncogene accounts for a large number of tumors. Activating mutations of the ras gene itself occur in about 30% of all human tumors (Bos, J. L., 1989), primarily in pancreatic (90%), sporadic colorectal (50%) and lung (40%) carcinomas, as well as myeloid leukemia (30%). In addition to mutations of the ras gene itself, activation of the factors upstream or downstream of ras in the ras pathway is also associated with tumors. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain. Altogether, direct mutation of the ras oncogene or an upstream element in the ras pathway is believed to occur in approximately two thirds of all tumors.

Given the significant role of the ras pathway in tumorigenesis, it is desirable to be able to determine if a tumor is associated with activation of the ras pathway so that a specifically tailored treatment regime may be developed. Prior to the present invention, however, there has not been a simple and sensitive method of diagnosing the association of a cancer with the ras pathway. While mutations in the ras structural gene may be detected with a high sensitivity by polymerase chain reaction (PCR), there are many other factors in the ras pathway which may be the cause of high ras activity, such as mutations in the ras gene flanking sequences which lead to abnormally high expression level of the ras gene product, mutations in the structural genes of a factor upstream or downstream of ras in the ras pathway, or regulatory mutations which affect the expression levels of these upstream or downstream factors. Therefore, PCR for the ras gene does not precisely identify all cancers associated with activation of the ras pathway. The need remains for a simple and precise method of diagnosing ras-activated tumors.

SUMMARY OF THE INVENTION

The present invention provides a method of diagnosing neoplasms having particular phenotypes, particularly neoplasms mediated by abnormally high activity of the ras pathway, by using reovirus or other similar oncolytic viruses. Reovirus does not replicate in normal cells. However, reovirus selectively replicates in cells with an activated ras pathway, which leads to death of these cells. The ras pathway in these cells may be activated due to mutations of the ras structural gene or abnormalities of any other factor in the ras pathway which lead to activation of the pathway. Therefore, a cell which becomes neoplastic due to, at least in part, elevated ras pathway activities can be diagnosed by its susceptibility to reovirus replication.

Accordingly, one aspect of the present invention provides a method of detecting ras-activated neoplastic cells in a biological sample, comprising contacting the sample with a reovirus and determining the ability of the reovirus to replicate in the sample, wherein the ability of the reovirus to replicate indicates the presence of ras-activated neoplastic cells in the sample.

The biological sample is preferably from a mammal, particularly a human. Any reovirus capable of replicating in ras-activated cells may be used in the present invention, for example a mammalian reovirus or an avian reovirus. The mammalian reovirus is preferably a serotype 3 reovirus and more preferably a Dearing strain reovirus.

In a preferred embodiment, the biological sample is from an animal bearing a neoplasm selected from the group consisting of lung cancer, prostate cancer, colorectal cancer, thyroid cancer, renal cancer, adrenal cancer, liver cancer, pancreatic cancer, breast cancer, hematopoietic cancer and central and peripheral nervous system cancer.

Another aspect of the present invention provides a method of diagnosing a ras-activated neoplasm in an animal, comprising:
 (a) removing a biological sample from the animal, wherein the sample comprises cells;
 (b) contacting the sample with a reovirus under conditions which allow the reovirus to replicate in ras-activated cells;
 (c) determining the ability of the reovirus to replicate in the sample; and
 (d) identifying the animal as having a ras-activated neoplasm if the reovirus can replicate in the sample.

The animal is preferably a mammal, particularly a human. Any reovirus capable of replicating in ras-activated cells may be used in the present invention, for example a mammalian reovirus or an avian reovirus. The mammalian reovirus is preferably a serotype 3 reovirus and more preferably a Dearing strain reovirus.

In a preferred embodiment, the biological sample is from an animal bearing a neoplasm selected from the group consisting of lung cancer, prostate cancer, colorectal cancer, thyroid cancer, renal cancer, adrenal cancer, liver cancer, pancreatic cancer, breast cancer, hematopoietic cancer and central and peripheral nervous system cancer.

Another aspect of the present invention provides a method of treating or ameliorating a ras-activated neoplasm in an animal, comprising:
 (a) identifying a ras-activated neoplasm in the animal by removing a group of cells from the animal, contacting the cells with a reovirus under conditions which allow the reovirus to replicate in ras-activated cells, and identifying the cells as comprising ras-activated neoplastic cells if the reovirus can replicate in the cells; and
 (b) administering to the animal an effective amount of a therapeutic agent-that is selective for ras-activated neoplasms.

The therapeutic agent that is selective for ras-activated neoplasms is preferably an oncolytic virus. The oncolytic virus is preferably a reovirus, an adenovirus mutated in the VA1 region, a vaccinia virus mutated in the K3L and/or E3L region, a parapoxvirus orf virus mutated in the OV20.0L gene, an influenza virus mutated in the NS-1 gene, a herpes virus mutated in the $\gamma_1 34.5$ gene, a vesicular stomatitis virus (VSV), or a Newcastle virus. Other therapeutic agents that are selective for ras-activated neoplasms include, without being limited to, farnesyl transferase inhibitors (FTIs) and RAF kinase inhibitors.

In any embodiment of the present invention, the reovirus may be a recombinant reovirus. The recombinant reovirus may be generated by co-infection of mammalian cells with different subtypes of reovirus. The recombinant reovirus may be naturally-occurring or non-naturally-occurring. The recombinant reovirus may be from two or more strains of reovirus, particularly two or more strains of reovirus selected from the group consisting of strain Dearing, strain Abney, strain Jones, and strain Lang. The recombinant reovirus may also result from reassortment of reoviruses from different serotypes, such as selected from the group consisting of serotype 1 reovirus, serotype 2 reovirus and serotype 3 reovirus. The recombinant reovirus may comprise naturally-occurring variant coat protein coding sequences or mutated coat protein coding sequences.

In addition to reovirus, a number of other oncolytic viruses are also selective for ras-activated neoplasms, and therefore they can be used to practice the present invention in the same manner as reovirus. These viruses include, without being limited to, adenoviruses mutated in the VA1 region, vaccinia viruses mutated in the K3L and/or E3L region, parapoxvirus orf viruses mutated in the OV20.0L gene, influenza viruses mutated in the NS-1 gene, or herpes viruses mutated in the $\gamma_1 34.5$ gene. Thus, for example, one aspect of the present invention provides a method of detecting ras-activated neoplastic cells in a biological sample, comprising contacting the sample with an oncolytic virus that selectively replicates in PKR-deficient cells, and determining the ability of the virus to replicate in the sample, wherein the ability of the virus to replicate indicates the presence of ras-activated neoplastic cells in the sample. Preferably, the oncolytic virus is selected from the group consisting of adenoviruses mutated in the VA1 region, vaccinia viruses mutated in the K3L and/or E3L region, parapoxvirus orf viruses mutated in the OV20.0L gene, influenza viruses mutated in the NS-1 gene, and herpes viruses mutated in the $\gamma_1 34.5$ gene.

Moreover, many other oncolytic viruses that are capable of selectively infecting particular tumor cells are also useful in the present invention in the same manner as reovirus. For example, vesicular stomatitis virus (VSV) can be used to diagnose interferon-resistant tumors, the ONYX-015 virus can be used to diagnose p53-deficient virus, and Delta24 virus can be used to diagnose Rb-deficient tumors. However, the oncolytic virus useful in the present invention is preferably not an adenovirus, particularly not the ONYX-015 virus.

Further provided by the present invention are methods of treating or ameliorating interferon-resistant tumors, p53-deficient tumors, or Rb-deficient tumors by first contacting a biological sample harvested from a tumor with a virus selected from the group consisting of VSV, ONYX-015 and Delta24, then treating the tumor with an appropriate therapeutic agent upon positive diagnosis.

Yet another aspect of the present invention provides a kit comprising a reovirus and a means for detecting replication of the reovirus. The detection means can be a pair of primers specific for the nucleic acid of the reovirus, and may optionally include reagents for PCR. The detection means can also be an antibody specific for a reovirus protein, as well as accompanying reagents such as secondary antibodies. The detection means can further be slides and dyes suitable for observing the morphology of infected cells under the microscope, or virus culture media and cells that can be used to determine the titer of the reovirus. Similarly, the present invention also provides kits comprising another virus capable of replicating in specific tumor cells, as well as means for detecting replication of the virus. Examples of these viruses include, without being limited to, VSV, ONYX-015 virus, and Delta24 virus.

Another aspect of this invention provides a kit comprising at least two viruses which can be used to phenotype tumors according to the present invention. The viruses are preferably selective for neoplasms with different phenotypes. Preferably, the viruses are selected from the group consisting of reovirus, VSV, the ONYX-015 virus, and the Delta24 virus.

Yet another aspect of this invention provides a kit comprising a virus useful for diagnosis of a neoplasm of a particular phenotype, as well as a therapeutic agent selective for the neoplasm.

Furthermore, since oncolytic viruses selectively replicate in neoplastic cells but not normal cells, another aspect of the present invention provides a method of diagnosing the presence of a neoplasm in a mammal, comprising contacting a sample of cells from said mammal with an oncolytic virus, wherein the ability of said virus to replicate in said sample indicates the presence of a neoplasm in said mammal.

Other aspects of the present invention would be evident in view of the entire disclosure of the present application.

DETAILED DESCRIPTION OF THE INVENTION

The present invention provides a method of diagnosing neoplasms having particular phenotypes by using oncolytic viruses. In particular, tumors mediated by abnormally high activity of the ras pathway can be diagnosed using reovirus. Reovirus does not replicate in normal cells. However, reovirus selectively replicates in cells with an activated ras pathway, which leads to death of these cells. Therefore, a ras-activated tumor can be diagnosed by its susceptibility to reovirus replication. The diagnosis will then facilitate the treatment or amelioration of the tumor with greater efficiency.

This invention can further be applied to diagnose and/or treat or ameliorate other tumors, such as interferon-resistant tumors, p53-deficient tumors and Rb-deficient tumors. Kits useful in the diagnosis or treatment disclosed herein are also provided.

Prior to describing the invention in further detail, the terms used in this application are defined as follows unless otherwise indicated.

Definitions

As used herein, "neoplastic cells", also known as "cells with a proliferative disorder", refer to cells which proliferate without the normal growth inhibition properties. A new growth comprising neoplastic cells is a "neoplasm" or "tumor". A neoplasm is an abnormal tissue growth, generally forming a distinct mass, that grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

A "PKR deficient cell" is a cell in which PKR is not activated as in normal cells. Such PKR deficiency may be due to, for example, a mutation in the PKR gene or a reduced level of PKR protein or activity. For example, ras-activated neoplastic cells are PKR deficient because the activated ras pathway blocks phosphorylated of PKR. Assays for PKR protein or activity levels are known in the art.

As used herein, "ras-activated neoplastic cells" or "ras-mediated neoplastic cells" refer to cells which proliferate at an abnormally high rate due to, at least in part, activation of the ras pathway. The ras pathway may be activated by way of ras gene structural mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or Sos results in activation of the ras pathway. Ras-mediated neoplastic cells include, but are not limited to, ras-mediated cancer cells, which are cells proliferating in a malignant manner due to activation of the ras pathway.

A "ras-activated tumor" is a tumor in which the ras pathway is activated.

An "interferon-resistant tumor" or "a tumor having the phenotype of interferon-resistance" is a tumor that can not be treated or ameliorated with interferon-alpha, beta or gamma.

A "p53-deficient tumor" or "a tumor having the phenotype of p53-deficiency" is a tumor in which the level of the cellular tumor suppressor p53 is lower than that in a normal cell.

An "Rb-deficient tumor" or "a tumor having the phenotype of Rb-deficiency" is a tumor in which the level of the cellular tumor suppressor Rb is lower than that in a normal cell.

An "oncolytic virus" is a virus that selectively kills neoplastic cells. Killing of the neoplastic cells can be detected by any method established in the art, such as determining viable cell count, cytopathic effect, apoptosis of the neoplastic cells, synthesis of viral proteins in the neoplastic cells (e.g., by metabolic labeling, Western analysis of viral proteins, or reverse transcription polymerase chain reaction of viral genes necessary for replication), or reduction in size of a tumor.

As used herein, "reovirus" refers to any virus classified in the reovirus genus. The name reovirus (Respiratory and enteric orphan virus) is a descriptive acronym suggesting that these viruses, although not associated with any known disease state in humans, can be isolated from both the respiratory and enteric tracts. The term "reovirus" refers to all viruses classified in the reovirus genus.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (See, for example, Nibert et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998) to reduce or prevent an immune response from a mammal which has developed immunity to the reovirus. For example, the virion may be treated with chymotrypsin in the presence of micelle forming concentrations of alkyl sulfate detergents to generate a new infectious subvirion particle.

The reovirus may be a recombinant reovirus resulting from the recombination/reassortment of genomic segments from two or more genetically distinct reoviruses. The recombinant reovirus may be from two or more types of reoviruses with differing pathogenic phenotypes such that it contains different antigenic determinants, thereby reducing or preventing an immune response by a mammal previously exposed to a reovirus subtype. Recombinant reoviruses may also exhibit different biological activities (e.g., replication activities in neoplastic cells and biodistribution) compared to the original reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses (Nibert et al. 1996).

Accordingly, the invention contemplates the use of recombinant reoviruses resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates the use of recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the use of recombinant reovirus that has undergone recombination in the presence of chemical mutagens, including but not limited to dimethyl sulfate and ethidium bromide, or physical mutagens, including but not limited to ultraviolet light and other forms of radiation.

The invention further contemplates recombinant reoviruses that comprise deletions or duplications in one or more genome segments, that comprise additional genetic information as a result of recombination with a host cell genome, or that comprise synthetic genes.

"Phenotyping" a tumor means classifying a tumor according to its phenotype. For example, tumor phenotypes include ras pathway activation, interferon-resistance, p53-deficiency and Rb-deficiency. The phenotypes are not mutually exclusive, namely, a tumor may be phenotyped into more than one class.

A "biological sample" is a sample collected from a biological subject, such as an animal.

An "effective amount" is an amount which is sufficient to achieve the intended purposes. For example, an effective amount of reovirus for the purpose of treating or ameliorating a disease or medical condition is an amount sufficient to result in a reduction or complete removal of the symptoms of a disease or medical condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Treating or ameliorating" a disease or medical condition means the reduction or complete removal of the symptoms of a disease or medical condition.

A therapeutic agent is "selective" for a particular disease or medical condition if the agent is more effective for the disease or medical condition than for other diseases or medical conditions. Similarly, a therapeutic agent is selective for a particular group of neoplastic cells if the agent kills the particular group of neoplastic cells with higher efficiency than other neoplastic cells.

Method

The present invention is useful in the precise phenotyping of tumors, thereby facilitating the development of a treatment regime that is tailored for a specific tumor. In a preferred embodiment, reovirus is used to infect a biological sample harvested from a tumor-bearing animal. Since reoviruses selectively infect ras-activated neoplastic cells but not normal cells or tumor cells in which the ras pathway is not activated, the present method enables the practitioner to precisely determine if the tumor is associated with ras pathway activation. If diagnosed to be ras activated, the tumor can then be treated with ras-specific treatment regimens, such as reovirus therapy (U.S. Pat. No. 6,136,307).

The ras pathway is a complex signal transduction pathway that leads to cellular proliferation. Ras is a central relay in this pathway, receiving signals from upstream elements (e.g., growth factor receptors) and transmitting them to downstream elements.

Many growth factor receptors such as epidermal growth factor (EGF) receptor, platelet-derived growth factor (PDGF) receptor, as well as EGF receptor-related molecules (e.g. Her-2/Neu/ErbB2), possess an intrinsic tyrosine kinase activity which is activated by ligand-induced receptor dimerization. This results in autophosphorylation of the receptor on tyrosine residues and the binding of proteins containing Src-homology 2 (SH2) domains. Two such SH2 proteins are Grb2 and SHC which indirectly activate the plasma membrane-associated, small GTP-binding protein Ras. Ras activation also occurs in response to ligand binding to seven transmembrane domain G-protein coupled receptors (e.g. Gutkind, 1998). Activation of Ras and other growth factor receptor-regulated signaling pathways ultimately leads to changes in the cytoskeleton and gene expression which are necessary for cellular proliferation, differentiation, and transformation (reviewed in Campbell et al., 1998).

The three human ras genes (Ha-Ras, N-Ras, and Ki-Ras) encode 4 proteins (due to alternative splicing of the Ki-Ras mRNA). Under normal circumstances, Ras proteins cycle between an active (GTP-bound) state and an inactive (GDP-bound) state. Ras activation occurs by exchange of bound GDP for GTP, which is facilitated by a family of guanine nucleotide exchange factors. Ras inactivation occurs by hydrolysis of bound GTP to GDP. This reaction is facilitated by GTPase activating proteins (GAPs). In many human cancers, Ras proteins become oncogenically activated by mutations which destroy their GTPase activity, and thus deregulate Ras signaling (reviewed in Campbell et al., 1998).

Multiple candidate Ras effectors exist that may serve downstream of Ras in signal transduction and oncogenic transformation, including members of the Rho family of small GTPases, phosphatidylinositol-3 kinase (PI3K) and the serine/threonine protein kinase c-Raf-1 (reviewed in Campbell et al., 1998). Raf-mediated signaling is the best characterized Ras effector pathway. Activated Ras recruits Raf to the membrane where Raf activation occurs. Activated Raf is the initial component of a kinase cascade, the Mitogen-Activated Protein Kinase (MAPK) cascade. Raf phosphorylates and activates the MEK1 and MEK2 (MAPK/ERK kinase) protein kinases which, in turn, phosphorylate and activate the Extracellular signal Regulated Kinases ERK1 and ERK2 (also known as MAPK1 and MAPK2). Unlike their downstream targets, ERK1,2, the MEK1,2 proteins are highly specific enzymes whose only known substrates are the ERK1,2 proteins. Upon activation, ERK1 and ERK2 phosphorylate (and thus regulate) a variety of target proteins, including nuclear transcription factors, leading to the ultimate cellular response.

Accordingly, numerous events can lead to activation of the ras pathway. For example, a mutation may occur in any of the three ras structural genes. Structural mutations may also take place in the receptors upstream of ras, the signal transducers downstream from ras (such as raf or mek1,2), or the ultimate effectors MAPK1 and 2. Similarly, regulatory mutations that lead to abnormally high levels of expression of any protein in the ras pathway may also cause mitogenic cellular responses. Such regulatory mutations may occur anywhere in the regulatory sequences of a ras pathway member, or even in the structural or regulatory region of a factor that controls the expression of a ras pathway member. Consequently, detection of aberration of any specific member in the ras pathway is not an efficient way to determine if the ras pathway is activated.

It is possible to measure the activity of MAPK, the ultimate effector of the ras pathway, since constitutive activation of MAPK is indicative of ras pathway activation. However, such a biochemical approach requires a substantial amount of sample material, as well as tedious procedures such as extraction and/or partial purification of MAPK.

By detecting the ras activated phenotype rather than aberration of any specific gene or gene product, the present invention is useful whether the ras pathway activation is due to mutation of the ras structural gene, regulatory sequences of the ras gene, or any other factor in the ras pathway. Furthermore, the present method is relatively simple, without the need to extract or purify an enzyme from the sample.

The ability of reovirus to infect cells in a sample can be determined by any method in the art. For example, reovirus nucleic acid replication can be measured by polymerase chain reaction with primers specific for the reovirus used; reovirus protein synthesis can be detected by specific antibodies; infected cells can be observed under a microscope and evidence of cytopathic effects induced by the reovirus detected; and replicated reovirus can be harvested from the sample, and virus titer determined, to assess if viral replication has taken place. Other methods of determining the presence of reovirus replication are known to or may be developed by people of ordinary skill in the art.

It should be noted that a tumor may contain multiple oncogenic abnormalities. In particular, it has been reported that ras activation is often preceded by p53 over-expression in breast cancer (Smith et al., 2000). The presence of other oncogenic abnormalities in addition to ras pathway activation, however, does not impede the ability of a therapy regime specifically tailored for ras-activated tumors. For example, reovirus can still selectively kill ras-activated neoplastic cells even if the cells also contain abnormally high levels of p53.

Furthermore, since reovirus selectively replicates in ras-activated neoplastic cells but not normal cells, another aspect of the present invention provides a method of diagnosing the presence of a neoplasm in a mammal, comprising contacting a sample of cells from said mammal with a reovirus under conditions that allow the reovirus to replicate in ras-activated cells, wherein the ability of said reovirus to replicate in said sample indicates the presence of a neoplasm in said mammal.

Similar to reovirus, a number of other oncolytic viruses also selectively replicate in ras-activated cells. It is contemplated that these oncolytic viruses can be employed to practice the present invention in the same manner as reovirus. These viruses typically are mutants that are sensitive to the double stranded RNA kinase (PKR), whereas their wild type counterparts are not sensitive to PKR.

Normally, when a virus enters a cell, PKR is activated and blocks protein synthesis, and the virus can not replicate in this cell. Some viruses have developed a system to inhibit PKR and facilitate viral protein synthesis as well as viral replication. For example, adenovirus makes a large amount of a small RNA, VA1 RNA. VA1 RNA has extensive secondary structures and binds to PKR in competition with the double stranded RNA (dsRNA) which normally activates PKR. Since it requires a minimum length of dsRNA to activate PKR, VA1 RNA does not activate PKR. Instead, it sequesters PKR by virtue of its large amount. Consequently, protein synthesis is not blocked and adenovirus can replicate in the cell.

Ras-activated neoplastic cells are not subject to protein synthesis inhibition by PKR, because ras inactivates PKR. These cells are therefore susceptible to viral infection even if the virus does not have a PKR inhibitory system. Accordingly, if the PKR inhibitors in adenovirus is mutated so as not to block PKR function anymore, the resulting virus does not infect normal cells due to protein synthesis inhibition by PKR, but they replicate in ras-activated neoplastic cells which lack PKR activities.

Accordingly, a virus that is modified or mutated such that it does not inhibit PKR function selectively replicates in ras-activated neoplastic cells while normal cells are resistant. Preferably, the virus is an adenovirus mutated in the VA1 region, a vaccinia virus mutated in the K3L and/or E3L region, a parapoxvirus orf virus mutated in the OV20.0L gene, an influenza virus mutated in the NS-1 gene, or a herpes virus mutated in the $\gamma_1 34.5$ gene.

The viruses can be modified or mutated according to the known structure-function relationship of the viral PKR inhibitors. For example, since the amino terminal region of E3 protein interacts with the carboxy-terminal region domain of PKR, deletion or point mutation of this domain prevents anti-PKR function (Chang et al., 1992, 1993, 1995; Sharp et al., 1998; Romano et al., 1998). The K3L gene of vaccinia virus encodes pK3, a pseudosubstrate of PKR. There is a loss-of-function mutation within K3L. Truncations or point mutations within the C-terminal portion of K3L protein that is homologous to residues 79 to 83 in eIF-2 abolish PKR inhibitory activity (Kawagishi-Kobayashi et al., 1997).

In another embodiment of the present invention, the vesicular stomatitis virus (VSV) can be used to diagnose interferon-resistant tumors. Interferons are circulating factors which bind to cell surface receptors and ultimately lead to both an antiviral response and an induction of growth inhibitory and/or apoptotic signals in the target cells. Although interferons can theoretically be used to inhibit proliferation of tumor cells, this attempt has not been very successful because of tumor-specific mutations of members of the interferon pathway.

However, by disrupting the interferon pathway to avoid growth inhibition exerted by interferon, tumor cells may simultaneously compromise their anti-viral response. Indeed, it has been shown that VSV, an enveloped, negative-sense RNA virus, rapidly replicated in and killed a variety of human tumor cell lines in the presence of interferon, while normal human primary cell cultures were apparently protected by interferon. VSV can thus be used to diagnose interferon-resistant yet VSV-sensitive tumors. Like the reovirus embodiment, VSV-based diagnosis is an assessment of the phenotype and does not depend on the mechanism of interferon resistance.

In another embodiment of the present invention, the ONYX-015 virus can be used to diagnose p53-deficient tumors. p53 is a potent tumor suppressor, which is present in every cell and controls cell growth. Since viruses rely on the cellular proliferation machinery to replicate, they are subject to p53 regulation and can not over-replicate. Certain adenovirus, SV40 and human papilloma virus, however, include proteins which inactivate p53, thereby allowing their own replication (Nemunaitis 1999).

For adenovirus serotype 5 this protein is a 55 Kd protein encoded by the E1B region. If the E1B region encoding this 55 kd protein is deleted, as in the ONYX-015 virus (Bischoff et al, 1996; WO 94/18992), the 55 kd p53 inhibitor is no longer present. As a result, when ONYX-015 enters a normal cell, p53 functions to suppress cell proliferation as well as viral replication. Therefore, ONYX-015 does not replicate in normal cells. On the other hand, in neoplastic cells with disrupted p53 function, ONYX-015 can replicate and eventually cause the cell to die. Accordingly, this virus can be used to detect p53-deficient neoplastic cells in a sample. A person of ordinary skill in the art can also mutate and disrupt the p53 inhibitor gene in adenovirus 5 or other viruses using established techniques, and the resulting viruses are useful in the present method to diagnose p53-deficient tumors.

Similarly, the Delta24 virus can be used to diagnose Rb-deficient tumors. The Delta24 virus is a mutant adenovirus carrying a 24 base pair deletion in the E1A region (Fueyo et al., 2000). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell. Accordingly, the Delta24 virus can be used to determine if a sample contains Rb-deficient tumor cells.

As is the case with the ras-activated tumor cells, p53-deficient or Rb-deficient cells may be the result of a variety of reasons. For example, a mutation in the structural gene of p53 or Rb may lead to a malfunctioning gene product or poor translation, a mutation in the regulatory sequence of the p53 or Rb gene may cause reduced amount of transcription, a mutation in a transcription factor for the p53 or Rb gene may result in deficient p53 or Rb production, or a mutation in a co-factor necessary for p53 or Rb function may also be the reason of p53- or Rb-deficiency. Since the present invention detects the phenotype, rather than structural aberration of the p53 or Rb gene/protein only, it is more powerful than structure-based methods, such as PCR.

Once the phenotype of a tumor has been determined, the tumor can be treated according to its phenotype. For example, a ras-activated tumor can be treated by reovirus, or inhibitors of the ras pathway. Accordingly, the present invention also provides a method of treating or ameliorating a ras-activated neoplasm in an animal, comprising identifying a ras-activated neoplasm in the animal by removing a group of cells from the animal, contacting the cells with a reovirus under conditions which allow the reovirus to replicate in ras-activated cells, identifying the cells as comprising ras-activated neoplastic cells if the reovirus can replicate in the cells, and administering an effective amount of reovirus to the mammal. Reovirus therapy has been disclosed, for example, in U.S. Pat. No. 6,136,307.

Furthermore, the present invention also provides methods of treating or ameliorating a tumor, comprising collecting a sample, identifying the phenotype of the sample with VSV, the Delta24 or ONYX-015 virus, and administering an effective amount of a suitable therapeutic agent according to the phenotype. The therapeutic agent may be the virus itself, or, in the case of p53 or Rb-deficiency, activators of p53 or Rb functions. It should be noted that Delta24 and ONYX-015 are merely examples to elucidate the application of the present invention, while a person with ordinary skill in the art will be able to identify or develop other viruses useful in the diagnosis and treatment of tumors according to the present disclosure.

As with reovirus, the use of immunoprotected or reassortant viruses of other oncolytic viruses are also encompassed in the present invention. Furthermore, in addition to the viruses specifically discussed in the present application, a person of ordinary skill in the art can practice the present invention using additional oncolytic viruses according to the disclosure herein and knowledge available in the art. The oncolytic virus may be a member in the family of myoviridae, siphoviridae, podoviridae, teciviridae, corticoviridae, plasmaviridae, lipothrixviridae, fuselloviridae, poxviridae, iridoviridae, phycodnaviridae, baculoviridae, herpesviridae, adenoviridae, papovaviridae, polydnaviridae, inoviridae, microviridae, geminiviridae, circoviridae, parvoviridae, hepadnaviridae, retroviridae, cyctoviridae, reoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, glaviviridae, togaviridae, or barnaviridae.

The present invention can be applied to any animal, particularly mammals. Preferred mammals include dogs, cats, sheep, goats, cattle, horses, pigs, humans and non-human primates. Most preferably, the mammal is human.

Kits

The present invention provides kits useful for the diagnosis and/or treatment of tumors. One aspect of the present invention provides a kit comprising a reovirus and a means for detecting replication of the reovirus. The detection means can be a pair of primers specific for the nucleic acid of the reovirus, and may optionally include reagents for PCR. The detection means can also be an antibody specific for a reovirus protein, and may optionally contain the accompanying reagents such as secondary antibodies. The detection means can further be slides and dyes suitable for observing the morphology of infected cells under the microscope, or virus culture media and cells that can be used to determine the titer of the reovirus. Similarly, the present invention also provides kits comprising another virus capable of replicating in specific tumor cells, as well as means for detecting replication of the virus. Examples of these viruses include, without being limited to, VSV, the ONYX-015, and Delta24 virus.

Another aspect of this invention provides a kit comprising at least two viruses which can be used to phenotype tumors according to the present invention. Preferably, the viruses are selected from the group consisting of reovirus, VSV, the ONYX-015 virus, and the Delta24 virus.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| °C. = | degree Celsius |
| hr = | hour |
| min = | minute |
| μM = | micromolar |
| mM = | millimolar |
| M = | molar |
| ml = | milliliter |
| μl = | microliter |
| mg = | milligram |
| μg = | microgram |
| PAGE = | polyacrylamide gel electrophoresis |
| rpm = | revolutions per minute |
| FBS = | fetal bovine serum |
| DTT = | dithiothrietol |
| SDS = | sodium dodecyl sulfate |
| PBS = | phosphate buffered saline |
| DMEM = | Dulbecco's modified Eagle's medium |
| α-MEM = | α-modified Eagle's medium |
| β-ME = | β-mercaptoethanol |
| MOI = | multiplicity of infection |
| PFU = | plaque forming units |
| EGF = | epidermal growth factor |
| PDGF = | platelet derived growth factor |
| CPE = | cytopathic effect |
| VSV = | vesicular stomatitis virus |
| PCR = | polymerase chain reaction |
| SH2 = | src-homology 2 |

Example 1

Phenotyping a Tumor With Reovirus

A lump is found in a 65 year old woman when she has her regular mammogram. A sample is collected from the lump during biopsy and appears to be a malignant tumor. In order to determine if the tumor contains ras-activated cells, the sample is placed in cell culture and incubated with reovirus.

The Dearing strain of reovirus serotype 3 is propagated in suspension cultures of L-929 cells purified according to Smith (Smith et al., 1969) with the exception that β-mercaptoethanol (β-ME) is omitted from the extraction buffer. The particle/PFU ratio for purified reovirus is typically 100/1. The biopsy sample is minced in DMEM, incubated with reovirus for 2 hours at 37° C., changed to fresh DMEM plus 20% FBS, and cultured for 48 hours. Thereafter, the supernatant of the culture is collected and reovirus titer is determined. The result indicates that reovirus has replicated in the sample. Therefore, the breast tumor contains ras-activated tumor cells.

We claim:

1. A method of diagnosing a neoplasm in an animal by phenotype, comprising:
   (a) providing a biological sample from the animal, wherein the sample comprises neoplastic cells with one or more unknown phenotypes;
   (b) providing at least two oncolytic viruses, wherein each oncolytic virus selectively replicates in neoplastic cells having a known phenotype selected from the group consisting of ras pathway activation, interferon-resistance, p53-deficiency and Rb-deficiency; and wherein each of the at least two oncolytic viruses replicates in neoplastic cells having a known different phenotype;
   (c) contacting the neoplastic cells from the sample with each of the at least two oncolytic viruses under conditions which allow each oncolytic virus to selectively replicate in the neoplastic cells from the sample;
   (d) determining if each of the oncolytic viruses selectively replicates in the neoplastic cells from the sample; and
   (e) diagnosing a neoplasm in the animal as comprising cells of a known phenotype according to the ability of each of the oncolytic viruses to selectively replicate in the neoplastic cells from the sample.

2. The method of claim 1 wherein the animal is a mammal.

3. The method of claim 2 wherein the mammal is human.

4. The method of claim 1 wherein the at least two oncolytic viruses are selected from the group consisting of reoviruses, adenoviruses mutated in the VA1 region, vaccinia viruses mutated in the K3L and/or E3L region, parapoxvirus off viruses mutated in the OV20.0L gene, influenza viruses mutated in the NS-1 gene, herpes viruses mutated in the $\gamma_1 34.5$ gene, vesicular stomatitis virus, ONYX-015 virus and Delta24 virus.

5. The method of claim 4 wherein at least one of the oncolytic viruses is selected from the group consisting of reovirus, vesicular stomatitis virus, ONYX-015 virus and Delta24 virus.

6. The method of claim 5 wherein the reovirus is a mammalian reovirus.

7. The method of claim 6 wherein the mammalian reovirus is a serotype 3 reovirus.

8. The method of claim 7 wherein the serotype 3 reovirus is a Dearing strain reovirus.

9. The method of claim 5 wherein the reovirus is an avian reovirus.

10. The method of claim 1 wherein the animal has a neoplasm selected from the group consisting of lung cancer, prostate cancer, colorectal cancer, thyroid cancer, renal cancer, adrenal cancer, liver cancer, pancreatic cancer, breast cancer, hematopoietic cancer and central and peripheral nervous system cancer.

* * * * *

UNITED STATES PATENT AND TRADEMARK OFFICE
CERTIFICATE OF CORRECTION

| | |
|---|---|
| PATENT NO. | : 7,306,902 B2 |
| APPLICATION NO. | : 10/602024 |
| DATED | : December 11, 2007 |
| INVENTOR(S) | : Bradley G. Thompson and Matthew C. Coffey |

It is certified that error appears in the above-identified patent and that said Letters Patent is hereby corrected as shown below:

Title Page;
On the front page of the patent, left column, on the line beginning with "(73)",
   "Oncolyties" should read --Oncolytics--

At column 14, line 38, "parapoxvirus off viruses" should read
   --parapoxvirus orf viruses--

Signed and Sealed this

Twenty-ninth Day of April, 2008

JON W. DUDAS
*Director of the United States Patent and Trademark Office*